(12) United States Patent
Bachman

(10) Patent No.: US 8,999,405 B1
(45) Date of Patent: Apr. 7, 2015

(54) SMOKELESS TOBACCO SUBSTITUTE

(71) Applicant: Stephen E. Bachman, Canyon, TX (US)

(72) Inventor: Stephen E. Bachman, Canyon, TX (US)

( * ) Notice: Subject to any disclaimer, the term of this patent is extended or adjusted under 35 U.S.C. 154(b) by 0 days.

(21) Appl. No.: 14/165,382

(22) Filed: Jan. 27, 2014

Related U.S. Application Data

(60) Provisional application No. 61/756,958, filed on Jan. 25, 2013.

(51) Int. Cl.
    *A01N 65/00*      (2009.01)
    *A61K 36/899*      (2006.01)
    *A61K 31/465*      (2006.01)
    *A61K 36/82*      (2006.01)

(52) U.S. Cl.
    CPC ............. *A61K 36/899* (2013.01); *A61K 31/465* (2013.01); *A61K 36/82* (2013.01)

(58) Field of Classification Search
    None
    See application file for complete search history.

(56) References Cited

U.S. PATENT DOCUMENTS 4,887,620 A * 12/1989 Summers ...................... 131/352

\* cited by examiner

*Primary Examiner* — Michael Meller
(74) *Attorney, Agent, or Firm* — Dale F. Regelman; Quarles & Brady LLP

(57) ABSTRACT

A smokeless tobacco substitute which includes a carrier and nicotine, wherein a plant-derived material has been steeped in hot water, and wherein a water-insoluble material is separated from the hot water and dried to form the carrier.

1 Claim, No Drawings

US 8,999,405 B1

SMOKELESS TOBACCO SUBSTITUTE

CROSS-REFERENCE TO RELATED APPLICATIONS

This is a Non-Provisional Application claiming priority to a United States Provisional Patent Application having Ser. No. 61/756,958 filed Jan. 25, 2013, which is hereby incorporated by reference herein.

FIELD OF THE INVENTION

Embodiments generally relate to a smokeless tobacco substitute (snuff, dip, chew, etc.); and more particularly, to a nontobacco snuff; and most particularly to a nontobacco snuff comprising a nicotine salt.

BACKGROUND OF THE INVENTION

Tobacco smoking is known to be linked with serious respiratory, heart, and neoplastic diseases. In 2010, the United States Surgeon General reported that annually, approximately one in every five deaths (443,000) in the United States was due to cigarettes. A large proportion of these deaths were caused by early heart attacks, chronic lung diseases, and cancers, which impose an economic burden of about $193 billion, annually, in health care costs and loss of productivity.

Tobacco smoke is an extremely complex mixture of about 6000 chemical compounds, which can be divided into two phases: a particulate phase, which is commonly called tar; and a vapor phase, which contains gases and semi-volatile compounds. About 4800 compounds have been identified in the tar portion of cigarette smoke and about 69 of these have been identified as carcinogens. At least 28 chemicals in smokeless tobacco have been found to cause cancer. The most harmful chemicals in smokeless tobacco are tobacco-specific nitrosamines, which are formed during the growing, curing, fermenting, and aging of tobacco. The level of tobacco-specific nitrosamines varies by product. Scientists have found that nitrosamine level is directly related to the risk of cancer. In addition, using smokeless tobacco may also cause heart disease, gum disease, and oral lesions.

Despite the dangers, many people persist in using tobacco products because of their addiction to nicotine, which constitutes about 0.6-3.0% of the dry weight of tobacco. In fact, nicotine dependence is higher than that of any other substance abuse disorder.

It would, therefore, be desirable to have a tobacco substitute that satiates a nicotine craving while minimizing exposure to the harmful compounds found in tobacco.

SUMMARY OF THE INVENTION

In certain embodiments, smokeless tobacco substitute includes nicotine and/or one or more nicotine salts. In certain embodiments, the smokeless tobacco substitute further includes a carrier derived from a plant material.

DETAILED DESCRIPTION OF THE PREFERRED EMBODIMENTS

The invention is described in preferred embodiments in the following description with reference to the Figures, in which like numerals represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Nicotine addiction is affected by the amount of nicotine and rate of nicotine absorption into the body. The higher the concentration and rate, the more addictive. Cigarettes produce one of the highest peak venous nicotine concentrations and most rapid absorption rates among nicotine products, such as chewing tobacco, and nicotine patch products. Table 1.0 recites, for each of a plurality of products, the amount of nicotine absorbed (bioavailability) per unit dose of product and respective time to reach maximum blood concentration of nicotine. The variation in the pharmacokinetics of nicotine among these products is due largely to the pH of its physiological environment.

TABLE 1.0

| Product | Bioavailability per dose | Time to maximum concentration in Venous Blood |
|---|---|---|
| Cigarette | 1-2 mg | Within 5 minutes |
| Nicotine gum (2 mg, 4 mg) | 1 mg, 2 mg | 30 minutes |
| Nicotine inhaler | 2 mg/cartridge | 20-30 minutes |
| Nicotine nasal spray | 0.5 mg | 10 minutes |
| Nicotine patch | 15-22 mg (during 16-24 hours) | 4-9 hours |
| Smokeless tobacco | 3.6-4.5 mg | 20-30 minutes |

For example, smoking tobacco rapidly delivers nicotine in the lungs because of the absorption of the nicotine smoke through the large alveoli surface area and the dissolution of nicotine in pulmonary fluid, which has an alkaline physiological pH that facilitates absorption. On the other hand, nicotine from oral products is more gradually absorbed. If swallowed, the nicotine enters the stomach and there is poorly absorbed due to the acidic environment. Nicotine from oral products that are maintained in the mouth, have a greater bioavailability than those that are not maintained in the mouth due to absorption through the oral mucosa, thereby entering the circulatory system before passing through the liver.

Commercial nicotine products, such as those listed in Table 1.0, include free base nicotine I.

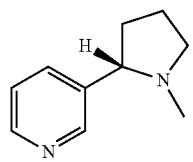

Free base nicotine, 3-(1-methyl-2-pyrrolidinyl) pyridine, is a naturally occurring nitrogenous base. Given its structure, nicotine has the ability to form salts with almost any acid and double salts with many metals and acids.

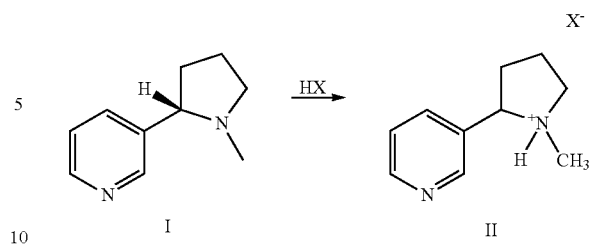

For example, when an acid HX reacts with an alkaline nitrogenous base of nicotine I (about pKa=8.5), a nicotine salt II is formed that has a lower pH (more acidic) than the free base due to the ionized state of nicotine. In certain embodiments HX acetic acid, formic acid, salicylic acid, and the like. In certain embodiments, $X^-$ is acetate, formate, salicylate, and the like.

Table 2.0 recites the physical characteristics of exemplary nicotine salts including their respective molar ratio and solubility in various solvents.

TABLE 2.0

| Acid | Melting Point (a) or begin to decompose (b) in °C. | Molar ratio of acid : nicotine | Solubility | | |
|---|---|---|---|---|---|
| | | | Water | Alcohol | Other |
| 2-Methylbutyric | | 3 : 1 | soluble | soluble | |
| 3-Methylbutyric | | 3 : 1 | soluble | soluble | |
| Acetic | | 3 : 1 | soluble | soluble | |
| Alginic | (b) > 160 | 1 : 1 | very soluble | insoluble | insoluble: ether |
| Aspartic | (a) > 300 | 1 : 1 | very soluble | insoluble | insoluble: ether |
| Benzoic | | 1 : 1 | soluble | soluble | |
| Butyric | | 3 : 1 | soluble | soluble | |
| Chloroptatinlc (C,0 H,.N, · PtCI · 2 HCI) | (b) > 250 | 1 : 1 | insoluble | insoluble | insoluble: ether |
| Citric | | 2 : 1 | soluble | soluble | |
| Formic | | 2 : 1 | soluble | soluble | |
| Gallic | 162-163 | 1 : 1 | soluble | soluble | insoluble: $CHCl_3$ |
| Gentisic | 147 | 1 : 1 | soluble | soluble | insoluble: $CHCl_3$, ethyl acetate |
| Glutamic | 199-200 | 1 : 1 | very soluble | soluble | insoluble: $CHCl_3$, ether |
| Hydrochloric | 154-55 | 2 : 1 | soluble | soluble | |
| Laurie | | 3 : 1 | insoluble | soluble | |
| Malic | 102-103 | 2 : 1 | soluble | soluble | |
| Oxalic | 110 | 2 : 1 | soluble | soluble | |
| Palmitic | | 3 : 1 | insoluble | soluble | |
| Pectic | (b) 200 (char at 240 oC) | 2 : 1 | soluble | insoluble | insoluble: ether |
| Phenylacetic | 113-114 | 3 : 1 | soluble | soluble | |
| Phthalic | 126-127 | 1 : 1 | soluble | soluble | insoluble: ether |
| Picric | 228-229 | 2 : 1 | insoluble | insoluble | insoluble: ether |
| Propionic | | 3 : 1 | soluble | soluble | |
| Pyruvic | | 2 : 1 | soluble | soluble | |
| Salicylic | 116-117 | 1 : 1 | soluble | soluble | soluble: ether |
| Sillcolungstic | stable > 300 | 1 : 1 | insoluble | soluble | insoluble: ether |

In certain embodiments, Applicant's smokeless tobacco substitute includes an acid addition salt solution of pharmaceutically active agents, such as nicotine. For example, a smokeless tobacco substitute includes a combined free base and one or more acid addition salt solution of nicotine (e.g., one or more salt recited Table 2.0), the combined composition of which enhances the penetration rates of nicotine into the body, more closely mimicking the absorption rates of smoking tobacco.

A nontobacco nicotine product including an acid addition salt of nicotine has a different pharmacokinetics than such having a free base nicotine alone. For example, a combination of a free base and an acid addition salt of nicotine results in a higher rate of permanent penetration through the stratum corneum or mucous membranes than the free base alone. Such a free base and acid addition salt disorders the lipid structure of the stratum corneum cell-envelopes in biological tissue. To illustrate, a solution containing equal parts of nicotine acetate and the free base is about three times more effective in inhibiting ciliary activity than a solution containing about 98% of the acetate.

Ideally, the pharmaceutically acceptable acid salts of nicotine are those that are non-toxic. Examples of non-toxic salts include salts containing pharmacologically acceptable anions, such as benzoate, benzenesulphonate, bitartrate, camphorate, ethanesulphonate, gluconate, hydrobromide, hydrochloride, hydroiodide, fumarate, maleate, methanesulphonate, nitrate, sulphate or bisulphate, pamoate, succinate, saccharate, p-toluene sulphonate, tartrate, and salicylate salts. In certain embodiments, the acid salt of nicotine is nicotine salicylate, $C_{17}H_{20}N_2O_3$, formed by reacting a free base form of nicotine with salicylic acid. Nicotine salicylate is a crystalline powder with a high nicotine content (approximately 54%) that is soluble in water and alcohol. A 10% aquatic solution of nicotine salicylate has a pH of about 5.5 to 6.0.

In certain embodiments, the smokeless tobacco substitute further includes a carrier for the nicotine. In certain embodiments, the carrier is not water soluble. In certain embodiments, a plant-derived material is steeped in water at about 200° F., with the water-insoluble material separated and solids dried to form the carrier.

In certain embodiments, the carrier is between 0 to about 99 weight percent of the overall composition of the smokeless tobacco substitute. In certain embodiments, the carrier is between about 50 to about 99 weight percent of the overall composition of the smokeless tobacco substitute. In certain embodiments, the carrier is between about 75 to abut 99 weight percent of the overall composition of the smokeless tobacco substitute.

In certain embodiments, the carrier comprises a tea leaf base. In certain embodiments, the carrier comprises a ground corn stalk base.

The carrier includes one or more ingredients. In certain embodiments, the carrier includes an ingredient selected from the group consisting of a conditioner, a medicament, a solvent, a preservative, a flavorant, a sweetener, and a combination thereof.

Depending on the desired organoleptic effect, the carrier is formulated to produce desirable properties in elasticity, texture, color, smell, or taste.

The following Examples are presented to further illustrate to persons skilled in the art how to make and use the invention. These examples are not intended as a limitation, however, upon the scope of the invention.

EXAMPLE IA

Preparation of Tea Leaves Base

1. Steep Tea. Using about a 10:1 ratio of 212° F. water to tea leaves, let steep for about three (3) minutes. Drain mixture through a #40 sieve (fine).

2. Cooking Steeped Tea-Making Tea Base. Pre-blend water and NaOH in a kettle. The final pH is very important, with a pH of between about 7.5 to about 7.9 being optimal. NaOH can be caustic to the mucosa. As a result, in certain embodiments $NaCO_3$ is used rather than NaOH.

Place steeped tea leaves, with other optional ingredients, into the kettle. Heat the kettle to 180 to 190° F. Cook mixture until most of the moisture has evaporated.

3. Dry Cooked Tea. Remove cooked tea from kettle and place a thin layer (¼ to ⅓ inch) onto a baking tray. Place tray in a convection oven and dry to a water activity of 0.80+/− 0.04 using a Vulcan Convection Oven at a Temperature of about 200° F., with an Air Flow setting of Low, and a Load set to 5.

4. Shredding. Applicant has discovered that getting the smokeless tobacco substitute composition to "pack" in the space between the lip and gum and not disperse around the oral cavity is critical. In certain embodiments, Applicant's snuff-like composition is shredded to produce long thin particles that will "pack."

In certain embodiments, the starting tea leaves are sieved to produce a desirable level of "shredding." Applicant has found that the sieved tea leaves show the desired "packing" In certain embodiments, the starting, sieved tea leaves comprise the size distribution recited in Table 3.0.

EXAMPLE IB

Preparation of Ground Corn Stalk Base

The procedure of Example IA is utilized with finely ground corn stalk material rather than tea leaves. Applicant's corn stalk material does not comprise, and should not be confused with, corn silk.

In certain embodiments, a plurality of mesh-sized starting corn stalk material is utilized. Table 3.0 recites the mesh sizes and weight percentages of corn stalk materials utilized.

TABLE 3.0

| MESH SIZE | WEIGHT PERCENT |
|---|---|
| >50 | 19.6 |
| 50 | 11.0 |
| 40 | 14.6 |
| 30 | 16.1 |
| 20 | 16.2 |
| 16 | 17.3 |
| 8 | 5.2 |

In certain embodiments, Applicant's tea leaves base comprises the following sieved

EXAMPLE II

Preparation of Unflavored Formulation

Using a tea leaves base of Example IA or a corn stalk base of Example IB, prepare an unflavored smokeless tobacco substitute using the following components.

| Ingredients | % |
| --- | --- |
| Tea Leaves Base | 78.00% |
| Glycerin | 20.0% |
| Nicotine Fluid | 2.00% |
| TOTAL | 100.00% |

Place Tea Leaves/Corn Stalk Base and Solka FLOC 900 in Hobart bowl and blend for 1 minute on speed 1. Preblend glycerin and nicotine liquid. While mixing, gradually pour glycerin mixture onto Tea Leaves Base. Continue mixing until all leaves are coated evenly, i.e. about 10 minutes at this scale.

EXAMPLE III

Preparation of a Tobacco Flavored Smokeless Tobacco Substitute

Using a tea leaves base of Example IA or a corn stalk base of Example IB, prepare a tobacco flavored smokeless tobacco substitute using the following components.

| Ingredients | % |
| --- | --- |
| Tea Leaves Base | 78.00% |
| Tobacco Flavorant | 1.00% |
| Glycerin | 19.00% |
| Nicotine Fluid | 2.00% |
| TOTAL | 100.00% |

Place Tea Leaves/Corn Stalk Base and Solka FLOC 900 in Hobart bowl and blend for 1 minute on speed 1. Preblend glycerin, nicotine liquid, and flavorant. While mixing, gradually pour glycerin mixture onto Tea Leaves Base. Continue mixing until all leaves are coated evenly, i.e. about 10 minutes at this scale.

EXAMPLE IV

Preparation of a Cayenne Flavored Smokeless Tobacco Substitute

Using a tea leaves base of Example IA or a corn stalk base of Example IB, prepare cayenne flavored smokeless tobacco substitute using the following components.

| Ingredients | % |
| --- | --- |
| Tea Leaves Base | 78.00% |
| Cayenne Flavorant | 1.00% |
| Glycerin | 19.00% |
| Nicotine Fluid | 2.00% |
| TOTAL | 100.00% |

Place Tea Leaves/Corn Stalk Base and Solka FLOC 900 in Hobart bowl and blend for 1 minute on speed 1. Preblend glycerin, nicotine liquid, and flavorant. While mixing, gradually pour glycerin mixture onto Tea Leaves Base. Continue mixing until all leaves are coated evenly, i.e. about 10 minutes at this scale.

EXAMPLE V

Preparation of a Mint 1 Flavored Smokeless Tobacco Substitute

Using a tea leaves base of Example IA or a corn stalk base of Example IB, prepare a Mint 1 flavored smokeless tobacco substitute using the following components.

| Ingredients | % |
| --- | --- |
| Tea Leaves Base | 78.00% |
| Mint Flavorant FAMB008 WILD | 1.00% |
| Glycerin | 19.00% |
| Nicotine Fluid | 2.00% |
| TOTAL | 100.00% |

Place Tea Leaves/Corn Stalk Base and Solka FLOC 900 in Hobart bowl and blend for 1 minute on speed 1. Preblend glycerin, nicotine liquid, and flavorant. While mixing, gradually pour glycerin mixture onto Tea Leaves Base. Continue mixing until all leaves are coated evenly, i.e. about 10 minutes at this scale.

EXAMPLE VI

Preparation of a Mint 2 Flavored Smokeless Tobacco Substitute

Using a tea leaves base of Example IA or a corn stalk base of Example IB, prepare a Mint 2 flavored smokeless tobacco substitute using the following components.

| Ingredients | % |
| --- | --- |
| Tea Leaves Base | 78.00% |
| Mint Flavorant FAM434 WILD | 1.00% |
| Glycerin | 19.00% |
| Nicotine Fluid | 2.00% |
| TOTAL | 100.00% |

Place Tea Leaves/Corn Stalk Base and Solka FLOC 900 in Hobart bowl and blend for 1 minute on speed 1. Preblend glycerin, nicotine liquid, and flavorant. While mixing, gradually pour glycerin mixture onto Tea Leaves Base. Continue mixing until all leaves are coated evenly, i.e. about 10 minutes at this scale.

While various embodiments have been described above, it should be understood that they have been presented by way of example only, not limitation and various changes in form and details may be made. Any portion of the apparatus, systems, and/or methods, for example, described herein may be combined in any combination, except mutually exclusive combinations. The embodiments described herein can include various combinations and/or sub-combinations of the functions, components and/or features of the different embodiments described.

Although the present invention has been described in detail with reference to certain embodiments, one skilled in the art will appreciate that the present invention can be practiced by other than the described embodiments, which have been presented for purposes of illustration and not of limitation.

Therefore, the scope of the appended claims should not be limited to the description of the embodiments contained herein.

I claim:

1. A smokeless gum or patch consisting essentially of a tea extract, glycerine, nicotine, and cayenne.

* * * * *